(12) United States Patent
Katz

(10) Patent No.: US 9,295,453 B2
(45) Date of Patent: Mar. 29, 2016

(54) BIOLOGICAL FLUID COLLECTION AND SAMPLING CONTAINER

(75) Inventor: Emil Katz, Savion (IL)

(73) Assignee: NOVAMED LTD., Jerusalem (IL)

( * ) Notice: Subject to any disclaimer, the term of this patent is extended or adjusted under 35 U.S.C. 154(b) by 2349 days.

(21) Appl. No.: 10/941,288

(22) Filed: Sep. 13, 2004

(65) Prior Publication Data

US 2005/0032239 A1    Feb. 10, 2005

Related U.S. Application Data

(63) Continuation-in-part of application No. PCT/IL02/00121, filed on Feb. 17, 2002.

(51) Int. Cl.
*G01N 33/00* (2006.01)
*A61B 10/00* (2006.01)

(52) U.S. Cl.
CPC ....... *A61B 10/007* (2013.01); *Y10T 436/25375* (2015.01)

(58) Field of Classification Search
CPC .......................................................... B01L 3/00
USPC ..................................... 422/50, 99, 100, 102
See application file for complete search history.

(56) References Cited

U.S. PATENT DOCUMENTS

| 4,116,066 A | 9/1978 | Mehl et al. |
|---|---|---|
| 4,300,404 A | 11/1981 | Mehl et al. |
| 4,927,605 A * | 5/1990 | Dorn et al. ............... 422/557 |
| 4,934,547 A | 6/1990 | Golias et al. |
| 5,312,009 A | 5/1994 | Ratajczak et al. |
| 5,318,550 A | 6/1994 | Cermak et al. |
| 5,329,644 A | 7/1994 | Scott |
| 5,334,348 A | 8/1994 | Saito et al. |
| 5,358,148 A | 10/1994 | Hanifl et al. |
| 5,380,289 A | 1/1995 | Hemstreet et al. |
| 5,388,699 A | 2/1995 | Ratajczak et al. |
| D358,468 S | 5/1995 | Howard |

(Continued)

FOREIGN PATENT DOCUMENTS

EP    0289761    11/1988

OTHER PUBLICATIONS

Written Statement Setting out the Grounds of Appeal, including: Claims (Main Request), Claims (Auxiliary Request 1) and Claims (Auxiliary Request 2), no date.

*Primary Examiner* — Sam P Siefke
(74) *Attorney, Agent, or Firm* — Roach Brown McCarthy & Gruber, P.C.; Kevin D. McCarthy

(57) ABSTRACT

A fluid collection and sampling container is disclosed, comprising; a cup member; a lid assembly removeably mounted to the cup member and having (a) on a location on the lid an aperture with closure means useful for introducing sampling means into the container without removing the lid assembly, and (b) on a further location on the lid a cannula and needle member useful for receiving an air evacuated tube and piercing its stopper. Furthermore a method is disclosed, for extracting a plurality of samples from a sampling container using alternate sampling methods which include extracting samples by means of evacuated tube and extracting samples by means of immersing extracting probe into liquid contained in the container, wherein there is no need in removal of the lid assembly or of other members from the cup during the extraction of samples through the use of the alternate sampling methods.

1 Claim, 1 Drawing Sheet

(56) References Cited

U.S. PATENT DOCUMENTS

| | | |
|---|---|---|
| 5,518,003 A | 5/1996 | Allan |
| D378,129 S | 2/1997 | Wexler et al. |
| 5,599,331 A | 2/1997 | Hemstreet et al. |
| 5,622,183 A | 4/1997 | Hazard et al. |
| 5,735,834 A | 4/1998 | Hemstreet et al. |
| 6,054,099 A | 4/2000 | Levy |
| 6,247,592 B1 * | 6/2001 | Racicot et al. ................ 206/366 |
| 6,315,145 B1 * | 11/2001 | Fask et al. .................. 220/254.1 |
| 6,783,019 B2 * | 8/2004 | Zettle et al. ................ 220/254.3 |
| 6,921,395 B2 * | 7/2005 | Carano et al. ................. 604/411 |
| 7,758,815 B2 * | 7/2010 | Hartselle ...................... 422/400 |
| 2003/0053938 A1 * | 3/2003 | Szeles .......................... 422/102 |

\* cited by examiner

BIOLOGICAL FLUID COLLECTION AND SAMPLING CONTAINER

This application is a continuation-in-part, which claims priority to of International Application No. PCT/IL02/00121 filed Feb. 17, 2002.

FIELD OF THE INVENTION

This invention relates to a specimen collection and sampling container for fluid specimens such as urine.

BACKGROUND OF THE INVENTION

At present, liquid specimen are usually collected in a container and covered with a lid and then send to the lab for analysis or put aside for later analysis.

It is often desired to divide a specimen into several aliquots (doses) so that each aliquot can be tested for different characteristics: for example one aliquot may be tested for enzymes, chemistry etc, and another—for culturing microorganism for count or identity.

For example, after at least one aliquot for a biochemistry test has been extracted, the remaining sample in the cup may be transferred to a bacteriological labwhere the lid has to be removed for extracting at least one additional aliquot and the test is done directly from the main cup, for example by using a dipslide—covered with semi solid culture media—which is dipped into the remaining sample, or a bacteriological loop is immersed into the sample and then cultured over agar plate.

Sampling for bacteriology test involves the following steps:

Removing the lid—using both hands
Putting the lid on the bench (upside sown)
Performing the test of choice The first two steps although simple—are hazardous as the liquid (e.g. urine) sample may be heavily contaminated, moreover, droplets from the lid may drop on the bench and the risk of contamination is increased.

U.S. Pat. No. 4,927,605 provides a specimen sampling device that collects a liquid specimen and segregates an aliquot of it away from the remaining portion of the specimen. The segregation is accomplished by closing the lid of the container after the sample collection. The aliquot is held within a separate compartment which may be comprised of an evacuated tube located within the container U.S. Pat. No. 4,300,404 describes a liquid collection container and a lid having a cannula and a needle member which extends into the lower end of the container and which cannula projects through the lid so as to enable to pierce the stopper of an air evacuated tube U.S. Pat. No. 6,054,099 discloses a sampling container having a lid with an aperture capped by a cap having integral hinge.

U.S. Pat. No. 6,315,145 discloses a sampling container having a lid with an aperture capped by a cap having an assembly hinge.

Non of said Patents discloses a sampling container having in one device both sampling arrangements of a port for extracting an aliquot without removal of the lid by receiving and piercing an evacuated tube, and an aperture with a cap, for extracting an aliquot by immersing a sampling probe such as a dipslide or a bacteriological loop through the aperture and into the sample, without removal of the lid.

U.S. Pat. No. 5,312,009 to Ratajczak et. al. discloses a sampling container having a lid (cover) 14 with a sampling port 22 and a removeable specimenn extractor 24 installed therein allowing for receiving an evacuated sampling tube (specimen vial) 34 for extracting a sample without removing the lid (cover) 14. A protrusion 38 is provided in the sample port 22 for engagement with the sample cup 26 of the removeable specimen extractor 24 for holding it in place until its removal is desired. According to Ratajczak et. al. it is possible to make use of both sampling arrangements, i.e. evacuated tube and a sampling probe to be immersed into the sample, without removal of the lid. There is a disadvantage however in Ratajczak invention, in that the order of sampling is predetermined such that samples to be extracted through evacuated tube should be extracted first, while samples to be extracted by immersing a sampling probe (i.e. without removal of the entire lid) could be performed only after removal of the removeable specimen extractor 24. Furthermore, in Ratajczak et. al. the sampling port 22 is covered by a threaded cap 20, which its removal and placing back between insertion of sampling probes (i.e. after discarding the removeable sample extractor 24) normally requires the use of both user hands. Actually, the lid (cover) 14 in Ratajczak et. al. is provided with a weight 46 at its bottom, to allow removing and placing the lid (cover) 14 on a horizontal surface 44 while assuring that the removed cover always rests on the horizontal surface in the orientation illustrated in FIG. 4 of Ratajczak et. al., thus avoiding a contact between the extraction tube 30 and the surface 44. This arrangement emphasizes the problem with the device of in Ratajczak et. al., which does not allow for taking samples in the two different sampling methods simultaneously without removing the lid.

ADDITIONAL REFERENCE PATENTS

U.S. Pat. No. 5,735,834; U.S. Pat. No. 5,622,183; U.S. Pat. No. 5,599,331; U.S. Pat. No. 5,518,003; U.S. Pat. No. 5,388,699; U.S. Pat. No. 5,380,289; U.S. Pat. No. 5,358,148; U.S. Pat. No. 5,334,348; U.S. Pat. No. 5,329,644; U.S. Pat. No. 5,318,550; D378,129; D358,468

OBJECTIVES OF THE INVENTION

One objective of the present invention is to simplify the opening step of the container for sampling Another objective of the present invention is to reduce the risk of contamination Yet a main and important aim of the present invention is to provide a device which will allow for either simultaneous or alternate use of both sample extraction methods, (namely by an evacuated tube and by immersing a sampling probe into the liquid contained in the cup), without requiring removal of the cup lid, and preferably without requiring the use of both user hands for reaching at the sample. By using a device which will allow for facilitating the sampling in such a manner, it is believed that the total average time spent for extracting all the required samples from a single sampling cup, will be reduced in between 5 and 30 seconds and more (depending on the number of samples to be taken, the extraction methods and devices, and the dexterity of the specific laboratory workers). It is appreciated that such relatively small reduction in the average period spent for treating of each cup, may be accumulated to significant lengths of time when dealing with high numbers such as hundreds, thousands, or tens of thousands of samples a day, as may be the situation in large laboratories.

SUMMARY OF THE PRESENT INVENTION

The present invention relates to a fluid collection and sampling container comprising; a cup member; a lid assembly removeably mounted to the cup member and having (a) on a location on the lid an aperture with closure means (in the context of the present invention referred to also as 'cap') useful for introducing sampling means into the container without removing the lid assembly, and (b) on a further location on the lid a cannula and needle member useful for receiving an air evacuated tube and piercing its stopper (the needle is hollow and is in liquid communication with a sample of liquid contained by the cup).

According to one embodiment of the present invention the cap is attached to the lid by an integral hinge.

According to another embodiment of the present invention the cap is attached to the lid by an assembly hinge.

The present invention further relates to a method for extracting a plurality of samples from a sampling container using alternate sampling methods (either simultaneously, or alternately) which include extracting samples by means of evacuated tube and extracting samples by means of imersing extracting probe into liquid contained in the container, the method comprising (not necessarily in the written order) (a) providing a sampling container having a cup member; a lid assembly removeably mounted to the cup member and having on a first location on the lid an aperture with closure means useful for introducing sampling means into the container without removing the lid assembly, and on a second location on the lid a cannula and needle member useful for receiving an air evacuated tube and piercing its stopper; (b) placing at least one time an avacuated tube in the cannula and piercing a stopper of the evacuated tube by the needle, then removing the tube with an extracted dose of sample; (c) uncapping the aperture by removing the closure means and inserting at least one time a sampling probe through the apperture, imersing the lower end of the probe in the liquid sample and removing the probe with an extracted sample dose captured by; (d) optionally capping the aperture by the closure means; (e) optionally transfering the sampling cup for another location where a sample is to be extracted; (f) repeating steps 'b' to 'e' a required number of times in a required number of locations (i.e. diferent laboratories or diferent testing positions in one laboratory, which the cup should be transported between them for extracting doses of samples), without removal of the lid assembly.

It should be noted that the order of said steps (b) and (c) may be reversed, and some times both steps could be performed simultaneously, i.e. while a dose of sample is extracted into the evacuated tube (according to step (b)) a quick worker may open the cap and perform step (c) or even repeat it for extracting several samples, then return to step (b) and remove the tube with the extracted sample.

By providing the sampling container of the present invention to the use of a plurality (and preferably to all) patient from which a sample should be collected and examined in predetermined laboratories, a significant processing time of the samplings could be saved, due to the accumulated amount of several (up to tens) of seconds that are saved in average per treatment time of each separate sampling container. Accordingly, the present invention relates also to a method for reducing the processing time of a plurality of liquid (e.g. urine) samples in biochemical and biological laboratories, the method comprising providing each of at least a part of a plurality of patients from which a liquid (e.g. urine) sample is to be collected with a sampling container having a cup member; a lid assembly removeably mounted to the cup member and having on a first location on the lid an aperture with closure means useful for introducing sampling means into the container without removing the lid assembly, and on a second location on the lid a cannula and needle member useful for receiving an air evacuated tube and piercing its stopper; (b) placing at least one time an avacuated tube in the cannula and piercing a stopper of the evacuated tube by the needle, then removing the tube with an extracted dose of sample; (c) uncapping the aperture by removing the closure means and inserting at least one time a sampling probe through the apperture, imersing the lower end of the probe in the liquid sample and removing the probe with an extracted sample dose captured by; (d) optionally capping the aperture by the closure means; (e) optionally transfering the sampling cup for another location where a sample is to be extracted; (f) repeating steps 'b' to 'e' a required number of times in a required number of locations without removal of the lid assembly.

The term 'liquid sample' relates to any biological source liquid, however, by a preferred embodiment the sample is urine.

DESCRIPTION OF THE PRESENT INVENTION

According to various embodiments the device according to the present invention relates to a fluid collection and sampling container comprising a cup member having a wide opening diameter, a lid assembly removably mounted to the cup member which lid member has an opening and a cover (cap) for closing the opening and useful for insertion of a sampling probe and immersing its lower end inside a liquid contained in the cup, and which lid member further has (on a different location than the opening) a cannula adapted for receiving an evacuated tube and piercing its stopper by a hollow needle located at a bottom end of the cannula and is in liquid communication with a liquid contained in the cup, such that a dose of a liquid could be extracted to an evacuated tube inserted to the cannula, without removal of the lid assembly from the cup. According to various embodiments of the present invention the cannula is irremovable from the lid and forms an integral part with the lid.

The aperture in the lid enables sampling from the container, by only removing the aperture cap and without removing the large lid member from the cup.

In accordance with one embodiment of the present invention the cap is attached to the lid via an integrated hinge.

In accordance with another embodiment of the present invention; the cover of the opening is made of a steaky sheet that can partially be unfolded to enable sampling yet remains partly attached to the lid.

In accordance with yet another embodiment of the present invention, the cap is attached to the lid by ring which is also attached to one side of the cap.

BRIEF DESCRIPTION OF DRAWINGS

In order to understand the invention and to see how it may be carried out in practice, an embodiment will now be described, by way of non-limiting example only, with reference to the accompanying drawings, in which.

DETAILED DESCRIPTION OF DRAWINGS

Figure 1:
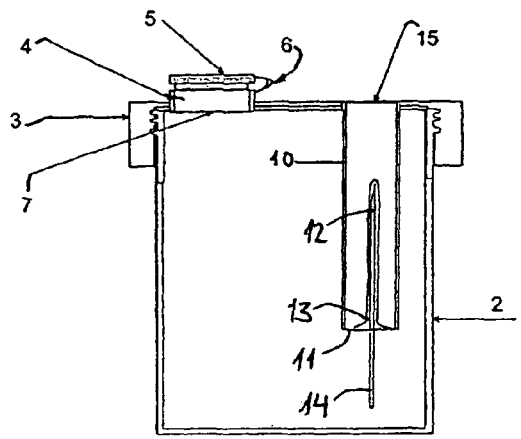
FIG. 1 is a vertical cross sectional view through a cup closed by a lid assembly, with an aperture on the lid in a capped state.
Figure 2:
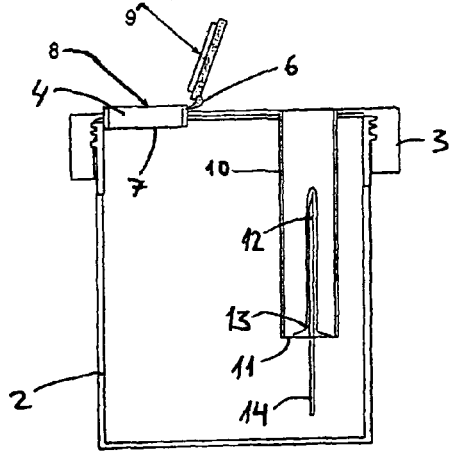
FIG. 2 is a vertical cross sectional view through a cup closed by a lid assembly, with an aperture on the lid in an uncapped state.

The device 1 according to one preferred embodiment is described in FIG. 1 where a collection cup 2 having a lid 3 (in the context of the present invention referred to also as 'lid assembly') removably attached (by threading means) to the upper opening of the cup 2, which lid 3 having a secondary opening 4 (in the context of the present invention referred to also as 'aperture') opened at its lower side 7 and at its upper side 8 (see FIG. 2) and can be closed by cap 5 which cap 5 is attached to the lid 3 via a integral hinge 6. Lid 3 also contains (on a different location from the opening 4) a sampling cannula 10 dedicated for sampling by using evacuated tube methodology.

In action lid 3 is first removed from the cup 2 so as to completely open cup 2, which then could be used for collection of sample 20 such as urine. After collection of the sample, the lid 3 is placed back on cup 2 and the device with the sample is transferred to the lab for analysis. From now on (and until final discarding of the sample and of the cup) there is no need to remove the lid 3 from the cup 2, since all the required sample extractions could be performed through the aperture 4, or through the cannula 10, by either insertion of a sampling probe to immerse inside the sample or insertion of an inverted evacuated tube into the cannula 10, which both could be performed either simultaneously or alternately any number of times according to the number of sample doses required.

At the lab, an aliquot for biochemistry can be drawn by inserting an evacuated test tube—upside down—into cannula 10 via opening 15, the needle 12 (that is a hollow needle) protruding from both sides of the bottom 11 of the cannula 10 and having a sharpened tip at its upper end, is forced to pierce both the apex of an elastic cover 13 protecting it as a sleeve and the elastic cap of the test tube (not shown), thus forming a communication between the test tube and the sample via the hollow needle which its lower end 14 (according to other embodiment the lower end of the needle is shorter, and is communicating with the liquid contained in the container through an extension pipe) is dipped in the liquid (not illustrated) contained by the cup 2, and an aliquot of the sample is drawn into the evacuated test tube.

The test tube could then be pulled out from the cannula, and the elastic cover 13 is reverted to the original position, the collection container is transferred to a bacteriology lab.

At the bacteriology lab, cap 5 is opened by pushing the end of it which is opposite to the hinge 6, such that cap 5 remains suspended and attached to the lid (see FIG. 2) through the hinge 6 and bacteriological tests can be performed via opening 4, without removing the lid 3, for example by using a sampling probe e.g. a dipslide—covered with semi solid culture media—the dipslide can be dipped into the remaining sample via opening 4, or e.g. a bacteriological loop can be immersed into the sample and then cultured over agar plate.

Figure 3:
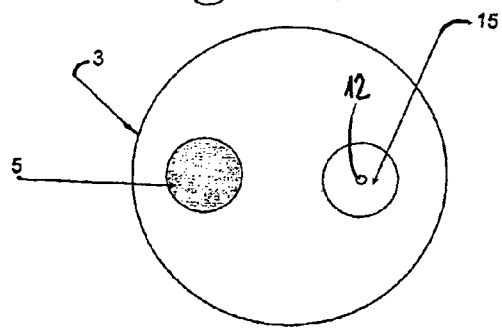
FIG. 3 is an upper view of the lid assembly.

FIG. 3 is an upper view of the lid assembly, comprising a cap 5 of the aperture 4 (hidden by the cap 5), and an opening 15 of the cannula with a needle 12 protruding from its bottom end.

Figure 4:
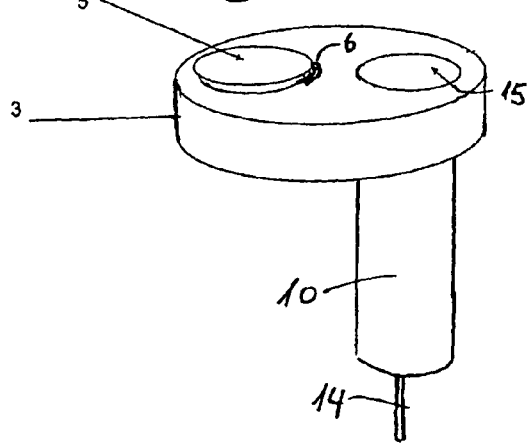
FIG. 4 is a perspective view of a lid assembly with the aperture on the lid in a capped state.

FIG. 4 is a perspective view of a lid assembly 3 with the aperture 4 (hidden in this Fig.) in a first location on the lid in a capped state, by cap 5. The cap 5 is secured to the lid 3 through integral hinge 6 which is connecting between the cap 5 and the lid 3. In a further location on the lid there is an opening 15 of cannula 10. In the illustrated embodiment the cannula forms an integral part with the lid 3. However, according to other embodiments of the invention the cannula my be fixed to the body of cup 2, wherein the lid 3 has an opening that fits with the opening of the cannula and further has mutual mechanism (such as protrusion and groove) with the cup which allow for positioning of the lid respective to the cup such that the opening in the lid will always be adjusted with the opening of the canula.

Figure 5:
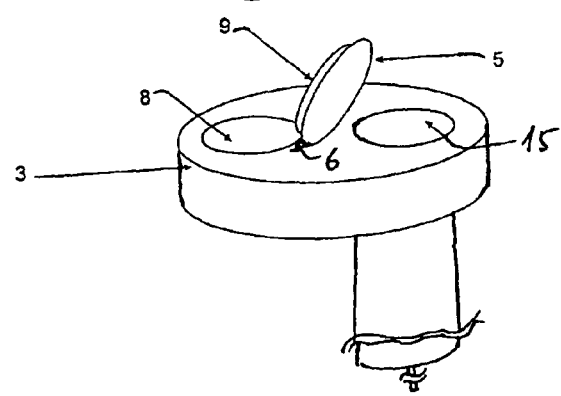
FIG. 5 is a perspective view of a lid assembly with the aperture on the lid in an uncapped state.

FIG. 5 is a perspective view of a lid assembly 3 with the aperture 4 on the lid in an uncapped state, wherein a sealing ring 9 could be observed at the bottom side of the cap 5, aimed to fit tightly over opening 8 which is the upper end of aperture 4.

In the illustrated embodiment the cannula forms an integral part with the lid 3. However, according to other embodiments of the invention the cannula my be fixed to the body of cup 2, wherein the lid 3 has an opening that fits with the opening of the cannula and further has mutual mechanism (such as protrusion and groove) with the cup which allow for positioning of the lid respective to the cup such that the opening in the lid will always be adjusted with the opening of the cannula when the lid is mounted on the cup. The bottom of the opening may be provided with a rim or a collar in order to form a sealed connection between the lid and the canulla which will allow no leakage from the cup through the opening.

In the illustrated embodiment the lid is secured to the cup by means of threading, however as could be appreciated, other connection method (e.g. fitting by pressure) could be implemented without departing from the scope of the present invention.

The invention claimed is:

1. A biological fluid collection and sampling container comprising a threaded cup member and a lid assembly attachable thereon, wherein said lid assembly comprises:
   (a) a first sampling port defining a substantially cylindrical chamber, irremovably provided with the lid, protruding from the bottom of which there is integrally provided a cannula-and-needle member suitable to pierce the stopper of an air evacuated tube; and
   (b) a second sampling port provided with an integrally hinged cap.

* * * * *